United States Patent
Dougherty (10) Patent No.: US 9,977,231 B2
(45) Date of Patent: *May 22, 2018

(54) OPTICAL MICROSCOPE AND METHOD FOR DETECTING LENS IMMERSION

(71) Applicant: General Electric Company, Schenectady, NY (US)

(72) Inventor: William Michael Dougherty, Issaquah, WA (US)

(73) Assignee: GENERAL ELECTRIC COMPANY, Wauwatosa, WI (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/430,975

(22) Filed: Feb. 13, 2017

(65) Prior Publication Data
US 2017/0153437 A1    Jun. 1, 2017

Related U.S. Application Data

(63) Continuation of application No. 14/788,035, filed on Jun. 30, 2015, now Pat. No. 9,599,807.

(51) Int. Cl.
| | |
|---|---|
| *G02B 21/24* | (2006.01) |
| *G01S 11/14* | (2006.01) |
| *G02B 21/34* | (2006.01) |
| *G02B 21/33* | (2006.01) |
| *G02B 21/02* | (2006.01) |

(52) U.S. Cl.
CPC ............ *G02B 21/247* (2013.01); *G01S 11/14* (2013.01); *G02B 21/02* (2013.01); *G02B 21/33* (2013.01); *G02B 21/34* (2013.01)

(58) Field of Classification Search
CPC ...... G02B 21/245; G02B 21/33; G02B 21/02; G02B 21/34; G01S 11/14; G01N 29/02
USPC ............................ 359/368–398; 73/606, 620
See application file for complete search history.

(56) References Cited

U.S. PATENT DOCUMENTS

| | | | | |
|---|---|---|---|---|
| 4,075,883 A | * | 2/1978 | Glover | A61B 8/0825 378/17 |
| 4,586,794 A | * | 5/1986 | Bierleutgeb | G02B 7/16 359/381 |
| 4,645,937 A | | 2/1987 | Atalar et al. | |
| 4,655,083 A | | 4/1987 | Chubachi | |
| 4,920,803 A | * | 5/1990 | Karaki | G01H 3/125 73/606 |
| 4,926,693 A | * | 5/1990 | Holm-Kennedy | B60G 17/01933 367/102 |

(Continued)

OTHER PUBLICATIONS

International Search Report and Written Opinion issued in connection with corresponding PCT Application No. PCT/US2016/37644 dated Sep. 16, 2016.

*Primary Examiner* — Frank Font
(74) *Attorney, Agent, or Firm* — Rong Zhang (57) ABSTRACT

An optical microscope and method for detecting lens immersion in optical microscopy includes an ultrasound circuit acoustically coupled to both an objective lens and a sample of an optical microscope, the ultrasound circuit comprising an ultrasound transmitter and an ultrasound receiver. The optical microscope and method includes transmitting an ultrasound pulse from the ultrasound transmitter to the ultrasound receiver, determining that a transit time of the ultrasound pulse is less than a threshold time, and providing an output signal from the pulse discriminator indicating that the ultrasound pulse is less than the threshold time.

26 Claims, 5 Drawing Sheets

(56) References Cited

U.S. PATENT DOCUMENTS

| | | | | |
|---|---|---|---|---|
| 4,966,038 A * | 10/1990 | Sakai | ............... | G01N 29/06 |
| | | | | 73/606 |
| 4,977,544 A * | 12/1990 | Karaki | ............... | G01N 29/06 |
| | | | | 367/7 |
| 5,062,297 A | 11/1991 | Hashimoto et al. | | |
| 5,121,634 A * | 6/1992 | Sasaki | ............... | G01H 3/125 |
| | | | | 73/606 |
| 5,406,849 A | 4/1995 | Drescher-Krasicka et al. | | |
| 6,720,876 B1 * | 4/2004 | Burgess | ............... | G01S 5/0289 |
| | | | | 340/10.1 |
| 9,618,445 B2 * | 4/2017 | Sun | ............... | G01N 21/1702 |
| 2002/0151767 A1 * | 10/2002 | Sonnenschein | ............... | A61B 1/0005 |
| | | | | 600/117 |
| 2003/0101820 A1 | 6/2003 | Siong | | |
| 2004/0125437 A1 * | 7/2004 | Schmidt | ............... | A61B 90/36 |
| | | | | 359/368 |
| 2008/0225278 A1 * | 9/2008 | Namba | ............... | G01N 21/6458 |
| | | | | 356/123 |
| 2009/0251691 A1 * | 10/2009 | Shibata | ............... | G02B 21/33 |
| | | | | 356/237.5 |
| 2010/0027109 A1 * | 2/2010 | Liebel | ............... | G02B 21/24 |
| | | | | 359/381 |
| 2011/0082590 A1 * | 4/2011 | Fahlbusch | ............... | G02B 7/023 |
| | | | | 700/275 |
| 2012/0330157 A1 * | 12/2012 | Mandella | ............... | G02B 21/0028 |
| | | | | 600/443 |
| 2013/0047719 A1 | 2/2013 | Knowles | | |
| 2014/0360273 A1 | 12/2014 | Zhang et al. | | |
| 2015/0316510 A1 * | 11/2015 | Fukushima | ............... | G02B 21/002 |
| | | | | 73/643 |
| 2016/0305914 A1 * | 10/2016 | Wang | ............... | G02B 21/0004 |

* cited by examiner

OPTICAL MICROSCOPE AND METHOD FOR DETECTING LENS IMMERSION

CROSS-REFERENCE TO RELATED APPLICATION

The present application is a continuation of, and claims priority to, U.S. patent application Ser. No. 14/788,035, filed Jun. 30, 2015, the disclosure of which is incorporated herein by reference in its entirety.

FIELD OF THE INVENTION

This disclosure relates generally to an optical microscope and method for detecting when an objective lens and a sample slide are both in direct contact with an immersion fluid.

BACKGROUND OF THE INVENTION

In optical microscopy, particularly in high resolution optical microscopy, an immersion fluid with a specific index of refraction is used in the working space between an objective lens and a sample slide. Using an immersion fluid with an index of refraction that is greater than air's index of refraction and closer to the objective lens's index of refraction enables the collection of more light with the objective lens, and results in improved resolution for the optical microscope.

When using an immersion fluid such as immersion fluid, it is imperative that the objective lens and the sample slide are both in direct contact with the immersion fluid. The presence of an air gap between the sample slide and the objective lens significantly decreases the advantage of using an immersion fluid. While it is critical to position both the objective lens and sample slide close enough to each other so that both are in contact with the immersion fluid, it is equally important to keep the objective lens from directly contacting the sample slide. Direct contact between the sample slide and the objective lens may result in damage to one or both of the sample and the objective lens. The objective lens is a key component of an optical microscope, and it is expensive to replace. Additionally, samples may be difficult, expensive, and time-consuming to prepare for imaging.

During a typical workflow, the distance between the objective lens and the sample slide is adjusted to bring the optical microscope into focus. During the process of focusing the optical microscope, it is often difficult for the operator to accurately determine whether the objective lens and the sample slide are both in direct contact with the immersion fluid. As discussed above, it is desirable to eliminate the air gap between the sample slide and the objective lens yet avoid causing the objective lens to make direct contact with the sample slide. The exact thickness of the sample is highly variable on the scale of many micrometers. As such, it is not possible to accurately predict the focus height of the objective lens with respect to each unique sample.

For these and other reasons, an improved optical microscope and method of determining lens immersion in optical microscopy is desired.

BRIEF DESCRIPTION OF THE INVENTION

The above-mentioned shortcomings, disadvantages, and problems are addressed herein which will be understood by reading and understanding the following specification.

In an embodiment, a method for detecting lens immersion in optical microscopy includes providing an ultrasound circuit acoustically coupled to both an objective lens and a sample slide of an optical microscope, the ultrasound circuit comprising an ultrasound transmitter and an ultrasound receiver, where the ultrasound circuit is configured to provide a first acoustic path, through a body of the optical microscope, when the objective lens and the sample slide are not both in direct contact with an immersion fluid and a second, shorter, acoustic path, through the immersion fluid, when the objective lens and the sample slide are both in direct contact with the immersion fluid. The method includes transmitting an ultrasound pulse from the ultrasound transmitter to the ultrasound receiver, determining with a pulse discriminator that a transit time of the ultrasound pulse is less than a threshold time, where the threshold time is selected to determine whether the pulse was transmitted along the first acoustic path or the second acoustic path, and providing an output signal from the pulse discriminator indicating that the ultrasound pulse is less than the threshold time in order to indicate that the objective lens and the sample slide are both in direct contact with the immersion fluid.

In an embodiment, a method for detecting lens immersion in optical microscopy includes providing an ultrasound circuit acoustically coupled to both an objective lens and a sample slide of an optical microscope, the ultrasound circuit comprising an ultrasound transmitter and an ultrasound receiver, where the ultrasound circuit is configured to provide a first acoustic path, through a body of the optical microscope, when the objective lens and the sample slide are not both in direct contact with an immersion fluid and a second, shorter, acoustic path, through the immersion fluid, when the objective lens and the sample slide are both in direct contact with the immersion fluid. The method includes transmitting a plurality of ultrasound pulses from the ultrasound transmitter to the ultrasound receiver, determining with a pulse discriminator if a transit time for each of the plurality of ultrasound pulses is either greater than or less than a threshold time, where the threshold time is used to identify whether each of the plurality of ultrasound pulses traveled along the first acoustic path or the second acoustic path, providing output signals from the pulse discriminator indicating whether the transit time for each of the plurality of ultrasound pulses is shorter or longer than the threshold time, and automatically adjusting a distance between the objective lens and the sample slide based on the output signals in order to position both the objective lens and the sample slide in direct contact with the immersion fluid.

In an embodiment, an optical microscope includes an objective lens, a slide holder configured to receive a sample slide, immersion fluid deposited on at least one of the objective lens and the sample slide, and a body connected to the objective lens and the slide holder. The optical microscope includes an adjustment mechanism attached to the body and configured to adjust a distance between the objective lens and the sample slide in the slide holder, an ultrasound circuit acoustically coupled to the objective lens and the sample slide in the slide holder, the ultrasound circuit comprising an ultrasound transmitter and an ultrasound receiver, where the ultrasound circuit is configured to provide a first acoustic path through a body of the optical microscope when the objective lens and the sample slide are not both in direct contact with an immersion fluid and a second, shorter, acoustic path, through the immersion fluid, when both the objective lens and the sample slide are in direct contact with the immersion fluid. The optical microscope includes a pulse discriminator electrically connected to the ultrasound circuit, wherein the pulse discriminator is configured to determine if a transit time of each ultrasound pulse transmitted between the ultrasound transmitter and the ultrasound receiver is less than a threshold time, where the threshold time is selected to identify whether the ultrasound pulse traveled along the first acoustic path or the second acoustic path, and wherein the pulse discriminator is configured to provide output signals indicating if the transit time of each ultrasound pulse is shorter or longer than the threshold time.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which are shown by way of illustration specific embodiments that may be practiced. These embodiments are described in sufficient detail to enable those skilled in the art to practice the embodiments, and it is to be understood that other embodiments may be utilized and that logical, mechanical, electrical, and other changes may be made without departing from the scope of the embodiments. The following detailed description is, therefore, not to be taken as limiting the scope of the invention.

Figure 1:
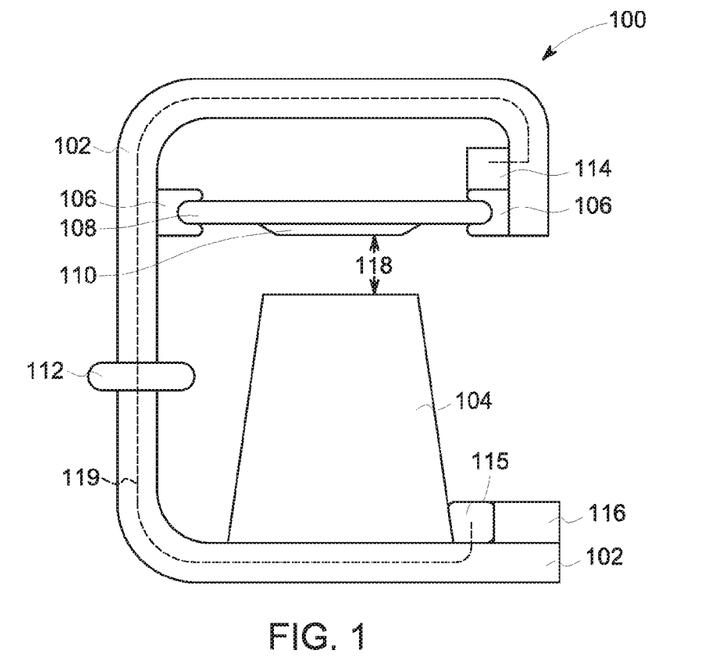
FIG. 1 is a schematic representation of an optical microscope in accordance with an exemplary embodiment.

FIG. 1 is a schematic representation of an optical microscope 100 in accordance with an exemplary embodiment. The optical microscope 100 includes a body 102, an objective lens 104, a slide holder 106, and a sample slide 108. For purposes of this disclosure, the term "slide" is defined to include a glass or plastic slide either with or without a coverslip, a microtiter well array, a flow cell, or any other fixture configured to hold or support a sample for observation with the optical microscope 100. The body 102 may be made from metal, such as an aluminum or steel alloy, a plastic, or the body may be made from any other material that transmits ultrasound energy. The body 102 may be either directly or indirectly connected to both the objective lens 104 and the slide holder 106, which is adapted to receive the sample slide 108. Both the objective lens 104 and the sample slide 108 are acoustically coupled to the body 102. For purposes of this disclosure, the term "acoustically coupled" is defined to include two or more structures or components that are attached in a manner configured to transmit ultrasound, or acoustic, energy. The slide holder 106 is configured to receive a sample slide such as the sample slide 108. The slide holder 106 may be configured to clamp down on the sample slide 108 to hold it in place as shown in FIG. 1, or the slide holder 106 may be configured to receive the sample slide 108 so that the sample slide 108 is held in place primarily by gravity. The sample slide 108 may include a coverslip (not shown in FIG. 1) that may be glued or otherwise affixed to a glass substrate. According to other embodiments, the sample slide 108 may not include a coverslip. The sample slide 108 may comprise a microtiter plate containing a plurality of individual samples according to other embodiments.

FIG. 1 includes a drop of immersion fluid 110 placed on the sample slide 108. The immersion fluid 110 may be an immersion oil with an index or refraction of about 1.5 according to an exemplary embodiment. Other embodiments may use another type of immersion fluid with a different index of refraction. For example, fluids such as water and glycerin may be used in other embodiments. It may be generally desirable to select an immersion fluid with an index of refraction that is larger than the index of refraction for air (approximately 1) and close to the index of refraction of the objective lens 104 according to some embodiments.

An adjustment mechanism 112 is connected to the body 102 and configured to adjust the distance between the objective lens 104 and the sample slide 108. The adjustment mechanism 112 may include a manual mechanism, such as a screw or worm-drive configured to be manually adjusted by the user, or the adjustment mechanism 112 may include an automatic or a semi-automatic mechanism. For example, the adjustment mechanism 112 may include a stepper motor, a piezoelectric control mechanism, a hydraulic circuit, or any other mechanism that may be used to adjust the position of the objective lens 104 with respect to the sample slide 108. It should be noted that the microscope 100 shown in FIG. 1 has an inverted geometry; the objective lens 104 is positioned beneath the sample slide 108. However, it should be appreciated that other embodiments may include microscopes with standard geometries, i.e., where the objective lens is positioned above the sample slide.

The optical microscope 100 also includes an ultrasound transmitter 114 and an ultrasound receiver 115. The ultrasound transmitter 114 is acoustically coupled to the sample slide 108, and the ultrasound receiver 115 is acoustically coupled to the objective lens 104 according to the embodiment shown in FIG. 1. The ultrasound transmitter 114 is in direct contact with the body 102 and the slide holder 106 in the embodiment shown in FIG. 1, but the ultrasound transmitter 114 may be in direct contact with the sample slide 108 according to other embodiments. The ultrasound receiver 115 is shown in direct contact with the objective lens 104 in the optical microscope 100, but in other embodiments, the ultrasound receiver 115 may be acoustically coupled to the objective lens 104 via one or more additional components.

The optical microscope 100 includes an ultrasound circuit comprising the ultrasound transmitter 114, the ultrasound receiver 115, and the first acoustic path 119. The first acoustic path 119, which is indicated in a dashed line, represents the path that ultrasound pulses travel from the ultrasound transmitter 114 to the ultrasound receiver 115 in the embodiment depicted in FIG. 1. The positions of the ultrasound transmitter 114 and the ultrasound receiver 115 may be switched according to other embodiments. For example, in other embodiments, an optical microscope may include an ultrasound receiver positioned where the ultrasound transmitter 114 is positioned in FIG. 1; and the optical microscope may include an ultrasound transmitter positioned where the ultrasound receiver 115 is positioned in FIG. 1. All embodiments must include an ultrasound circuit acoustically coupled to the sample slide 108 and the objective lens 104. The ultrasound transmitter 114 must be spaced apart from the ultrasound receiver 115. The purposes of the ultrasound transmitter 114 and the ultrasound receiver 115 will be described in greater detail hereinafter. The optical microscope 100 also includes a pulse discriminator 116 electrically connected to the ultrasound circuit. The pulse discriminator 116 may receive data from the ultrasound receiver 115. The pulse discriminator 116 may be an electrical circuit according to an embodiment. The pulse discriminator 116 may also include a processor according to other embodiments.

FIG. 1 shows the optical microscope in a position where the objective lens 104 is not in contact with the immersion fluid 110, as noted by the presence of an air gap 118 between the objective lens 104 and the immersion fluid 110 in contact with the sample slide 108. Those skilled in the art should appreciate that the acoustic transmission through the air for ultrasound signals with frequencies in the 1-50 MHz range is very close to zero.

Figure 2:
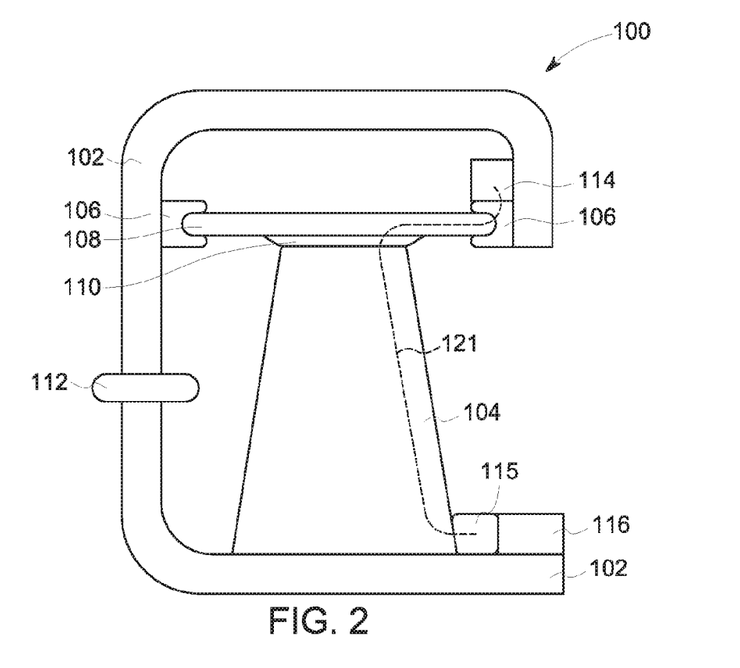
FIG. 2 is a schematic representation of an optical microscope in accordance with an exemplary embodiment.

FIG. 2 is a schematic representation of the optical microscope 100 in accordance with an exemplary embodiment. Common reference numbers are used in both FIGS. 1 and 2 to identify identical components.

The optical microscope 100 in FIG. 2 is represented in a position where the objective lens 104 and the sample slide 108 are both in direct contact with the immersion fluid 110. As such, the adjustment mechanism 112 may be positioned differently in FIG. 2 than in FIG. 1. The adjustment mechanism 112 may directly control the position of the sample slide 108, and/or the adjustment mechanism 112 may directly control the position of the objective lens 104. According to other embodiments, the adjustment mechanism 112 may adjust some or all of the body 102 in order to control the relative position of the sample slide 108 with respect to the objective lens 104.

Figure 3:
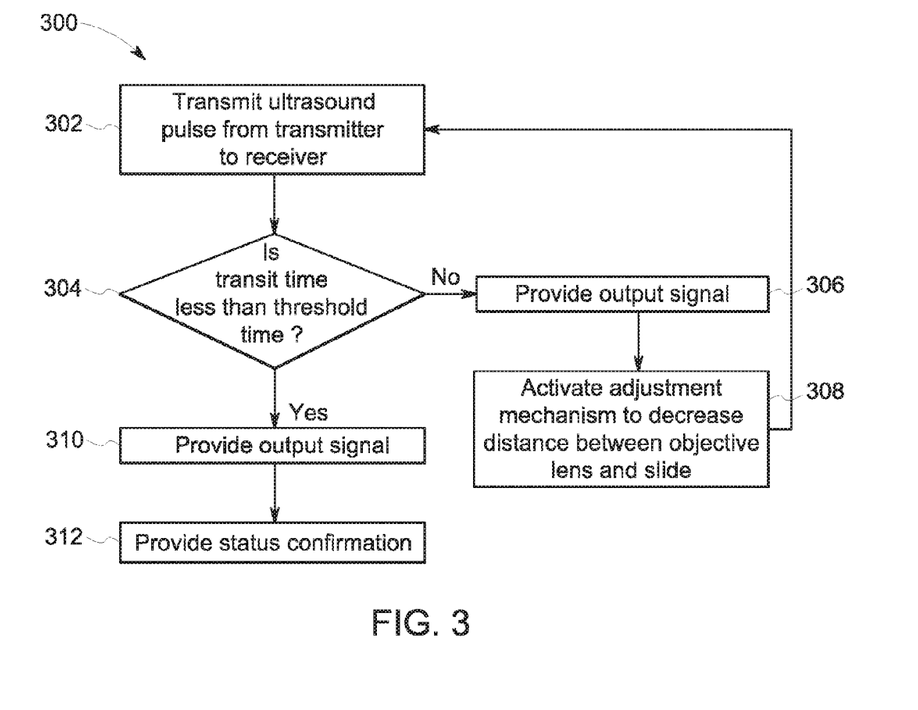
FIG. 3 is a flow chart of a method in accordance with an exemplary embodiment.

FIG. 3 is a flow chart of a method 300 that may be performed in accordance with an exemplary embodiment. The individual blocks of the flow chart represent steps that may be performed in accordance with the method 300. Additional embodiments may perform the steps shown in a different sequence, and/or additional embodiments may include additional steps not shown in FIG. 3. The technical effect of the method 300 is determining if both an objective lens and a sample slide are in direct contact with immersion fluid through the use of ultrasound. The method 300 will be described according to an exemplary embodiment using the optical microscope 100 shown in FIGS. 1 and 2.

Referring to FIGS. 1, 2, and 3, at step 302, one or more ultrasound pulses that are transmitted from the ultrasound transmitter 114 to the ultrasound receiver 115. According to an exemplary embodiment, the ultrasound pulses may have a center frequency in the MHz range and may be repeated at a repetition rate of approximately 1 KHz. It should be appreciated that other embodiments may use ultrasound pulses with different center frequencies and/or different repetition rates.

Next, at step 304, timing data from the ultrasound circuit is provided to the pulse discriminator 116. The pulse discriminator 116 determines whether the transit time for each ultrasound pulse is less than a threshold time. FIG. 1 shows a configuration where the objective lens 104 is not in contact with the immersion fluid 110. When an ultrasound pulse is transmitted from the ultrasound transmitter 114, the ultrasound pulse cannot travel across the air gap 118 between the immersion fluid 110 and the objective lens 104. Instead, the ultrasound pulse must travel through the body 102 of the microscope 100 in order to reach the ultrasound receiver 115. The first acoustic path 119 represents the path that the ultrasound pulse will travel from the ultrasound transmitter 114 to the ultrasound receiver 115. The first acoustic path 119 represents one potential acoustic path through the body of the optical microscope 100. However, it should be appreciated that other embodiments may have different acoustic paths. The transit time, or time it takes for the ultrasound pulse to travel from the transmitter 114 to the receiver 115, is determined based on the length of the acoustic path. FIG. 2, in contrast, shows a configuration where the sample slide 108, and the objective lens 104 are in direct contact with the immersion fluid 110. As such, an ultrasound pulse transmitted from the transmitter 114 may travel through the slide holder 106, the sample slide 108, the immersion fluid 110, the objective lens, and the frame in order to reach the receiver 115. The time required for an ultrasound pulse to travel along the first acoustic path 119, as described with respect to FIG. 1, will be measurably longer than the time required for the ultrasound pulse to travel along the second acoustic path 121 through the immersion fluid 110, as described with respect to FIG. 2, since the first acoustic path 119 is significantly longer than the second acoustic path 121. The transit time for an exemplary microscope along the first acoustic path 119 through the body 102 may be approximately 40 μS. In contrast, the transit time for the ultrasound pulse traveling along the second acoustic path 121, which travels through the immersion fluid 110, may be about 15 μS. Therefore, the target time may be between 15 μS and 25 μS according to an embodiment. Other embodiments may empirically determine the value of the target time depending upon the specific configuration of the optical microscope. The ultrasound circuit should be configured so that the there is a measurable difference in transit times for ultrasound pulses depending upon whether they travel through the body 102 (as represented by the first acoustic path 119, as shown in FIG. 1) to reach the receiver 115 or through the immersion fluid 110 (as represented by the second acoustic path, as shown in FIG. 2). According to the embodiment described with respect to FIGS. 1 and 2, the threshold time may be selected so that ultrasound pulses will have to travel through the immersion fluid 110 in order to be shorter than the threshold time. Those skilled in the art will appreciate that the exact placements of the ultrasound transmitter 114 and the ultrasound receiver 115 in the ultrasound circuit will affect the value selected for the threshold time.

If the transit time is not less than the threshold time, the method 300 advances to step 306. On the microscope 100 shown in FIGS. 1 and 2, transmitting the pulse through the immersion fluid 110, such as by the second acoustic path 121, represents a shorter path, and therefore a shorter time, from the transmitter 114 to the receiver 115. Therefore, having a transit time that is longer than the threshold time would indicate that the ultrasound pulse traveled a longer path because the objective lens 104 and the sample slide 108 are not both in direct contact with the immersion fluid 110.

At step 306, the pulse discriminator 116 provides an output signal indicating that the transit time is longer than the threshold time. According to an embodiment, the signal may be a specified voltage or TTL level. It should be appreciated that any other type of output signal may be used according to other embodiments.

At step 308, the adjustment mechanism 112 is activated in response to receiving the output signal from the pulse discriminator in order to decrease the distance between the objective lens 104 and the sample slide 108. The adjustment mechanism 112 may be operated manually by an operator. The output signal may also be used to first trigger a status indicator. For example, status indicators such as a light, a text-based message, an audible tone, or a recorded message may be used to indicate that the operator needs to make an adjustment. According to other embodiments, a status indicator may not be displayed. The adjustment mechanism may decrease the distance between the sample slide 108 and the objective lens 104 until receiving confirmation that both the objective lens 104 and the sample slide 108 are both in contact with the immersion fluid 110. According to an embodiment, the operator may adjust a dial or screw in order to adjust the gap between the objective lens 104 and the sample slide 108.

According to an exemplary embodiment, the output signal from the pulse discriminator 116 may be used to automatically initiate movement of the adjustment mechanism 112. For example, the pulse discriminator 116 may provide an output signal indicating that the transit time is longer than the threshold time. This output signal may automatically trigger movement by the adjustment mechanism 112. According to another embodiment, the pulse discriminator may optionally include a processor, and the processor may automatically control the adjustment mechanism 112 to decrease the distance between the objective lens 104 and the sample slide 108 in response to determining that the transit time is greater than the threshold time.

After step 308, the method 300 returns to step 302. Steps 302, 304, 306, and 308 may be repeated as many times as necessary until the transit time is less than the threshold time. According to an exemplary embodiment, ultrasound pulses may be transmitted at regular intervals during the implementation of the method 300. If, at step 304, the transit time for the ultrasound pulse is less than the threshold time, the method 300 advances to step 310. At step 310, the pulse discriminator 116 provides an output signal to indicate that the transit time of the ultrasound pulse is less than the target time. In the case of the embodiment described with respect to FIGS. 1 and 2, having a transit time less than the threshold time indicates that the sample slide 108 and the objective lens are both in direct contact with the immersion fluid 110. Next, at step 312 a status confirmation is provided. The status confirmation may include playing an audible noise or tone through a speaker, displaying a text phrase or a light on a display device, haptic feedback, or any other technique for providing feedback in order to indicate that the objective lens 104 and the sample slide 108 are both in direct contact with the immersion fluid.

Though the method 300 shown in FIG. 3 includes the step 312 of providing a status confirmation, it should be appreciated that other embodiments, including fully automated embodiments, may not include the step 312 of providing a status confirmation. For example, it may not be necessary to provide a status confirmation if the control of the adjustment mechanism 112 is completely automatic.

Figure 4:
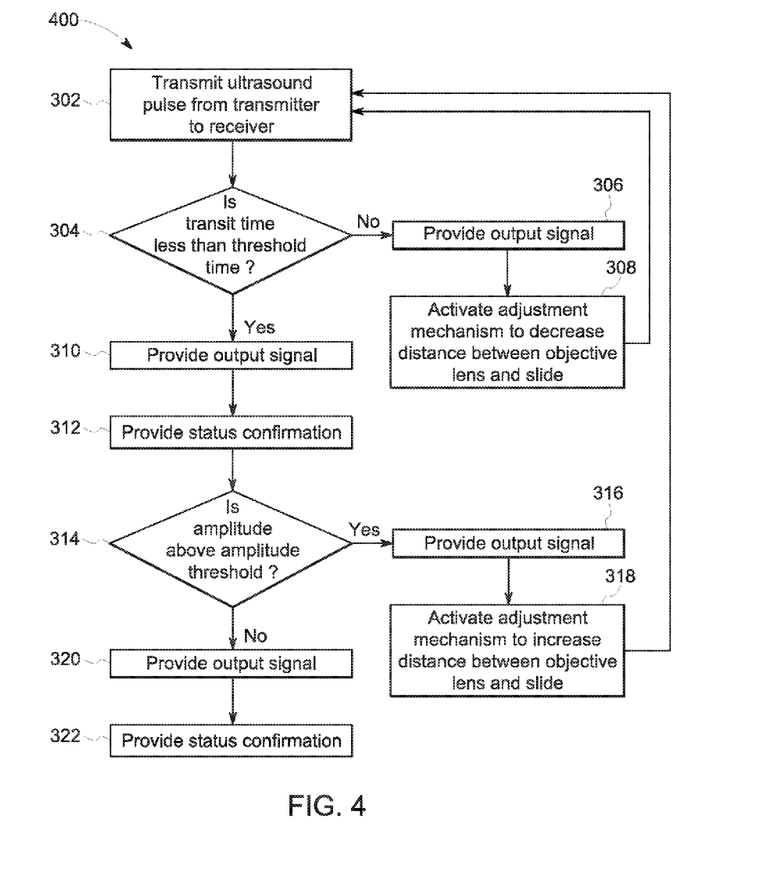
FIG. 4 is a flow chart of a method in accordance with an exemplary embodiment.

FIG. 4 is a flow chart of a method 400 that may be performed in accordance with an exemplary embodiment. The individual blocks of the flow chart represent steps that may be performed in accordance with the method 400. Additional embodiments may perform the steps shown in a different sequence, and/or additional embodiments may include additional steps not shown in FIG. 4. The technical effect of the method 400 is determining whether an objective lens and a sample slide are in direct contact with immersion fluid through the use of ultrasound. The method 400 will be described according to an exemplary embodiment using the optical microscope 100 shown in FIGS. 1 and 2. Many of the steps represented in FIG. 4 are identical to steps that were previously described with respect to FIG. 3. Steps that are identical between FIGS. 3 and 4 have been identified with identical reference numbers. Specifically, steps 302, 304, 306, 308, 310, and 312 represented in FIG. 4 are identical to the correspondingly numbered steps described with respect to FIG. 3. The description of the method 400 therefore starts at step 314.

After step 312, the method 400 advances to step 314. At step 314, the pulse discriminator 116 determines whether the amplitude of the ultrasound pulse is greater than an amplitude threshold. If the method 400 advances to step 314, the transit time of the ultrasound pulse is necessarily less than the threshold time based on step 304. Since the transit time is less than the threshold time, the ultrasound pulse is assumed to be following an acoustic path through the immersion fluid 110, similar to acoustic path 121, which was described with respect to FIG. 2. The amplitude threshold may be selected to indicate whether or not the objective lens 104 is in direct contact with the sample slide 108. It is undesirable to have the objective lens 104 in direct contact with the sample slide 108 for the reasons previously discussed during the background of the invention: specifically, there is significant risk of damaging the objective lens and/or ruining the sample on the sample slide 108. If the objective lens 104 is in contact with the immersion fluid but not in direct contact with the sample slide 108, some of the amplitude of the ultrasound pulse will be attenuated when the ultrasound pulse travels through the immersion fluid 110 since the immersion fluid is not as efficient of a conductor of sound as either the objective lens 104 or the sample slide 108. Therefore, an amplitude of the ultrasound pulse that is above the threshold amplitude would indicate that the objective lens 104 is in direct contact with the sample slide 108, which is undesirable. The threshold amplitude may be determined either theoretically based on the acoustic attenuation of the materials in the optical microscope 100, or it may be determined empirically. Initial experimentation has indicated that the amplitude of the ultrasound pulse received by the ultrasound receiver 115 may have an amplitude more than 2 orders of magnitude higher when there is direct contact of the objective lens 104 to the sample slide 108 compared to situations where the objective lens 104 and the sample slide 108 are not in direct contact with each other and the ultrasound pulse is transmitted through the immersion fluid 110. The threshold amplitude may vary based on the exact configuration of the optical microscope used for imaging. If the amplitude is greater than the amplitude threshold, the method advances to step 316.

At step 316, the pulse discriminator 116 provides an output signal indicating that the amplitude is above the amplitude threshold. The output signal may be a specified voltage or TTL level. It should be appreciated that any other type of signal may be used according to other embodiments. Next, at step 318, the output signal is used to activate the adjustment mechanism 112 to increase the distance between the objective lens 104 and the sample slide 108. The adjustment mechanism 112 may automatically move objective lens 104 a predetermined distance from the sample slide 108 after receiving the output signal at step 316. For example, the adjustment mechanism 112 may increase the distance so that there is a fixed amount of space, such as 300 μm, between the objective lens 104 and the sample slide 108. The adjustment mechanism 112 may be controlled to add a different amount of space according to other embodiments.

After step 318, the method 400 returns to step 302 where the previously described steps are performed an additional time.

If, at step 314, the pulse discriminator determines that the amplitude of the ultrasound pulse is not above the amplitude threshold, the method 400 advances to step 320. At step 320, the pulse discriminator 116 provides an output signal to indicate that the amplitude of the pulse is lower than the amplitude threshold. The output signal may be a specified voltage or TTL level. It should be appreciated that any other type of signal may be used according to other embodiments. Next, at step 322 the method 400 may provide a status confirmation to indicate that the amplitude is lower than the threshold amplitude. Since the transit time is less than the threshold time, as determined at step 304, and the amplitude is less than the threshold amplitude, the status confirmation displayed at step 322 indicates that the objective lens 104 is not in direct contact with the sample slide 108. When the method 400 reaches step 322, the optical microscope 100 is ready for final focusing and imaging of the sample.

Figure 5:
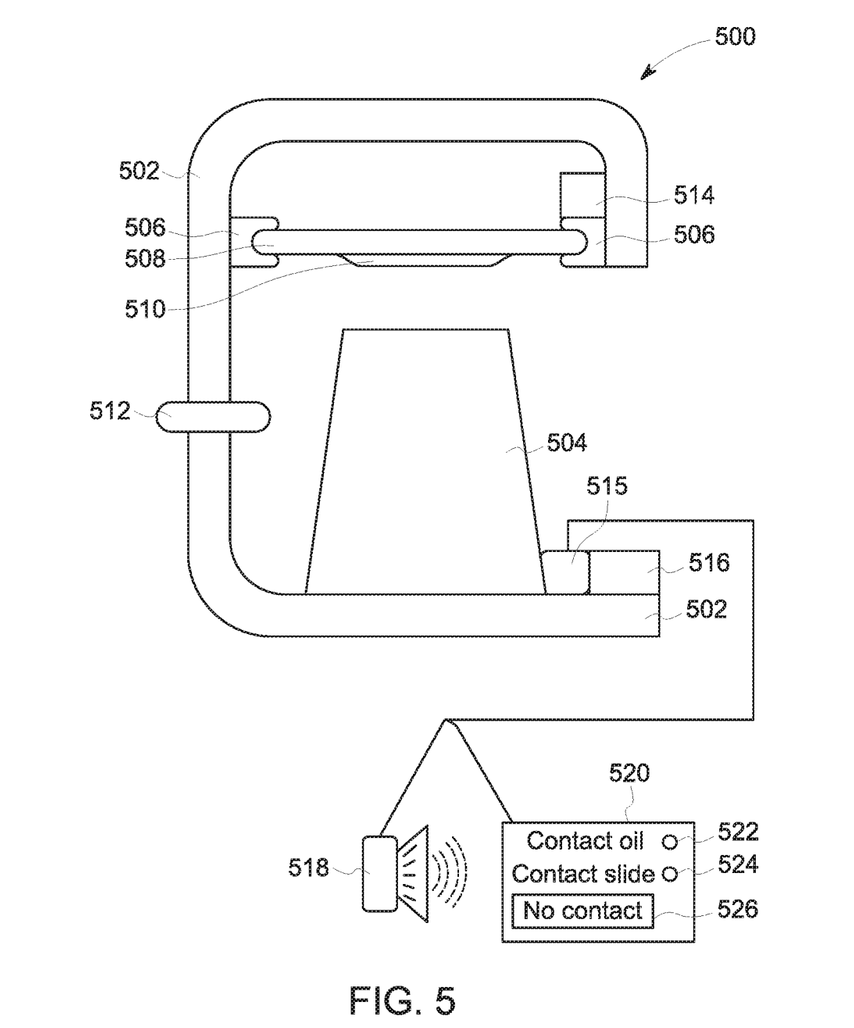
FIG. 5 is a schematic representation of an optical microscope in accordance with an exemplary embodiment.

FIG. 5 is a schematic representation of an optical microscope 500 in accordance with an embodiment. The optical microscope includes a body 502, an objective lens 504, a slide holder 506, a sample slide 508, a drop of immersion fluid 510, an adjustment mechanism 512, and an ultrasound circuit including an ultrasound transmitter 514, an ultrasound receiver 515, and a pulse discriminator 516. The body 502, the objective lens 504, the slide holder 506, the sample slide 508, the immersion fluid 510, the adjustment mechanism 512, the ultrasound transmitter 514, the ultrasound receiver 515, and the pulse discriminator 516 are all functionally equivalent to the identically named components that were previously described with respect to FIGS. 1 and 2, and will therefore not be described in detail with respect to FIG. 5. The optical microscope 500 additionally includes a speaker 518, a display device 520, a first light 522, and a second light 524. The speaker 518 and the display device 520 are both electrically connected to the pulse discriminator 516. The first light 522 and the second light 524 are both shown on the display device in FIG. 5, but one or more lights may be positioned on the optical microscope 500 in a location other than the display device 520 according to other embodiments.

The speaker 518, the display device 520, the first light 522, and the second light 524 may all be used to display one or more status indicators in accordance with an embodiment. As described with respect to FIGS. 3 and 4, the status indicators may be used to indicate the following statuses: the objective lens 504 and the sample slide 508 are not both in contact with the immersion fluid 510; the objective lens 504 and the sample slide 508 are both in contact with the immersion fluid 510; the objective lens 504 is not in direct contact with the sample slide 508; and the objective lens 504 is in direct contact with the sample slide 508.

The speaker 518 may be used to emit an audible noise, tone, or a recorded message in order to convey the status confirmation. For example, a first tone or a first recorded message may be used to confirm that the objective lens 504 and the sample slide 508 are both in direct contact with the immersion fluid 510. A second tone or second recorded message may be used to confirm that the objective lens 504 and the sample slide 508 are not both in direct contact with the immersion fluid 510. A third tone or a third recorded message may be used to confirm that objective lens 504 is not in direct contact with the sample slide 508. A fourth tone or a fourth recorded message may be used to confirm that the objective lens 504 is in direct contact with the sample slide 508.

In other embodiments, status confirmation may be provided by the use of the light. Lights of different colors, or lights positioned differently on the optical microscope or display device, may be used to provide a status confirmation for each of the previously described states. For example, the first light 522 may be used to indicate that the objective lens 504 and the sample slide 508 are both in direct contact with the immersion fluid 510. The first light 522 may be a first color, such as green, when both the objective lens 504 and the sample slide 508 are both in direct contact with the immersion fluid 510 and the light 522 may be a second color, such as red, when the objective lens 504 and the sample slide 508 are not both in direct contact with the immersion fluid 510. The second light 524 may be used to indicate that the objective lens 504 is in direct contact with the sample slide 508. The second light 508 may be red to indicate that the objective lens 504 is in direct contact with the sample slide 508 and green to indicate that the objective lens 504 is not in direct contact with the sample slide 508. It should be appreciated that other embodiments may use fewer lighter, more lights, and/or different conventions involving colors may be used to provide the various status confirmations. The display device 520 includes a text phrase 526. The text phrase 526 indicates, "no contact" indicating that the objective lens 504 and the sample slide 508 are not both in contact with the immersion fluid 510. Other text phrases may be displayed as the status changes or according to other embodiments.

It should be appreciated that some embodiments may provide status confirmations for only a few of the previously described states. For example, in an exemplary embodiment, it is anticipated that it may be beneficial to only show when the objective lens and the sample slide are both in contact with the immersion fluid, and to provide a status indicator warning the operator when the objective lens directly contacts the sample slide. Additionally, different status indicators may be provided in different manners according to various embodiments.

Figure 6:
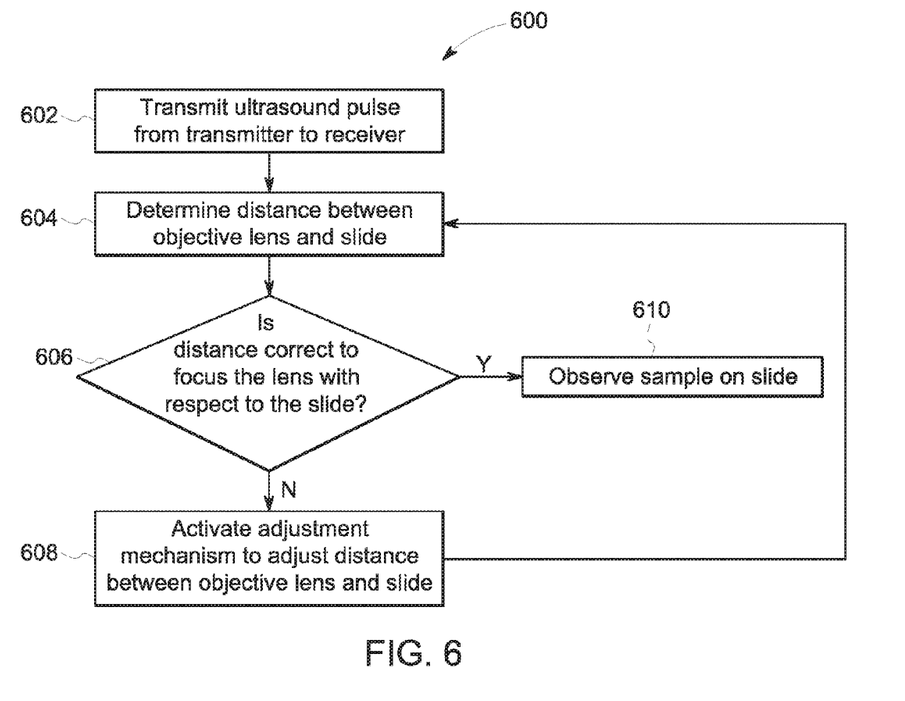
FIG. 6 is a flow chart of a method in accordance with an exemplary embodiment.

FIG. 6 is a flow chart of a method 600 that may be performed in accordance with an exemplary embodiment. The individual blocks of the flow chart represent steps that may be performed in accordance with the method 600. Additional embodiments may perform the steps shown in a different sequence, and/or additional embodiments may include additional steps not shown in FIG. 6. The technical effect of the method 600 is determining the distance between an objective lens and a slide based on one or more ultrasound pulses, and activating an adjustment mechanism to focus the objective lens with respect to the slide.

The method 600 will be described in conjunction with FIG. 1. At step 602, the ultrasound pulse is transmitted from the transmitter 114 to the receiver 115. The ultrasound pulse may be a single frequency pulse or the ultrasound pulse may be a spectral pulse including a spectrum of different frequencies. The spectrum may be complex and include, for instance, one or both of magnitude and phase components. According to an embodiment, the spectral pulse may be a chirped pulse. At step 604, the pulse discriminator 116 determines the distance between the objective lens 104 and the sample slide 108.

According to an embodiment where the ultrasound pulse is a single frequency, the pulse discriminator 116 may calculate the distance between the objective lens 104 and the sample slide 108 by measuring the decay of the ultrasound pulse. If the objective lens 104 and the sample slide 108 are both in contact with the immersion fluid, then the ultrasound pulse should exhibit roughly an exponential decay when traveling through the immersion fluid 110. The exact decay properties of the ultrasound pulse will depend on the frequency. The pulse discriminator 116 may determine the distance between the objective lens 104 and the sample slide 108 by comparing the strength of the signal to a model or by accessing a look-up table populated with experimentally determined or modeled decay values through given distances of immersion fluid 110. According to another embodiment, the pulse discriminator 116 may determine the distance by inputting the strength of the received ultrasound pulse into a formula to calculate the distance of immersion fluid 110 that the pulse traveled through in order result in the measured strength of the ultrasound pulse.

According to an embodiment where the ultrasound pulse is a spectral pulse, the pulse discriminator 116 may determine the distance between the objective lens 104 and the sample slide 108 by measuring how the various frequencies in the spectral pulse are attenuated as they travel through the immersion fluid 110. Since the higher frequencies in the spectral pulse are attenuated more than the lower frequencies, the shape of the received waveform will change based on the separation between the objective lens 104 and the sample slide 108. The pulse discriminator 116 analyzes the received waveform and determines the relative attenuation of the various component frequencies in the transmitted spectral pulse. The pulse discriminator 116 determines the distance between the objective lens 104 and the sample slide 108 based on the relative attenuation of the various frequencies in the received ultrasound pulse. The pulse discriminator 116 may input the attenuation values into a model to determine the amount of immersion fluid 110 between the objective lens 104 and the sample slide 108, or the pulse discriminator 116 may reference a look-up table to determine the distance between the sample slide 108 and the objective lens 104.

At step 606, the pulse discriminator 116 determines if the distance between the objective lens 104 and the sample slide 108 is correct to focus the objective lens 104 with respect to the sample slide 108. If the distance is not correct, the method 600 advances to step 608 where the pulse discriminator 116 activates the adjustment mechanism 112 to adjust the distance between the sample slide 108 and the objective lens 104. If the distance between the sample slide 108 and the objective lens 104 is too close, the adjustment mechanism 112 will increase the distance between the sample slide 108 and the objective lens 104. If the distance between the sample slide 108 and the objective lens 104 is too far, the adjustment mechanism 112 will decrease the distance between the sample slide 108 and the objective lens 104.

The method 600 may iteratively cycle through steps 604, 606, and 608 until the distance between the sample slide 108 and the objective lens 104 is correct to focus the objective lens 104 with respect to the sample slide 108. If the distance between the sample slide 108 and the objective lens 104 is correct to focus the objective lens 104 with respect to the sample slide 108 at step 606, the method 600 advances to step 610 where the sample on the sample slide 108 is observed. It should be appreciated that, according to other embodiments, a processor other than the pulse discriminator 116 may be used to in steps 604, 606, and 608 of the method 600. Additionally, the processor or the pulse discriminator 116 may employ spectral techniques measuring both magnitudes and phases according to an exemplary embodiment.

Figure 7:
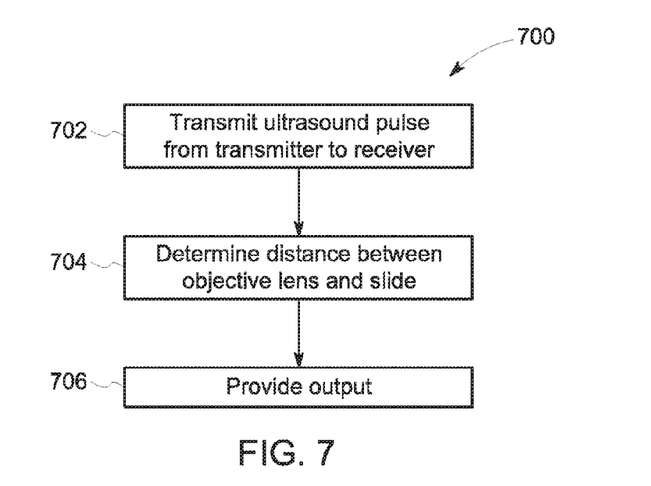
FIG. 7 is a flow chart of a method in accordance with an exemplary embodiment.

FIG. 7 is a flow chart of a method 700 that may be performed in accordance with an exemplary embodiment. The individual blocks of the flow chart represent steps that may be performed in accordance with the method 700. Additional embodiments may perform the steps shown in a different sequence, and/or additional embodiments may include additional steps not shown in FIG. 7. The technical effect of the method 700 is determining the distance between an objective lens and a slide based on one or more ultrasound pulses and providing an output based on the distance. The method 700 will be described in conjunction with the system 100 shown in FIG. 2.

At step 702, the transmitter 114 transmits an ultrasound pulse to the receiver 115. The ultrasound pulse may be either a single frequency pulse, or the ultrasound pulse may be a spectral pulse including a spectrum of different frequencies. The spectrum may be complex and include, for instance, one or both of magnitude and phase components. According to an embodiment, the spectral pulse may be a chirped pulse. At step 704, the pulse discriminator 116 determines the distance between the objective lens 104 and the sample slide 108. The pulse discriminator 116 may determine the distance between the objective lens 104 and the sample slide 108 through either of the techniques that were previously described with respect to step 604 of the method 600.

At step 706, the pulse discriminator 116 provides an output based on the distance that was calculated at step 704. The output may include displaying the distance, providing a warning when the distance is too close, or activating the adjustment mechanism 112 to prevent the objective lens 104 from colliding with the sample slide 108 during the process of moving the objective lens 104 closer to the sample slide 108. It should be appreciated that, according to other embodiments, a processor other than the pulse discriminator may be used to perform steps 704 and 706. Additionally, the processor or the pulse discriminator 116 may employ spectral techniques measuring both magnitudes and phases according to an exemplary embodiment.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they have structural elements that do not differ from the literal language of the claims or if they include equivalent structural elements with insubstantial differences from the literal language of the claims.

I claim:

1. A method for determining lens immersion in an instrument, the method comprising:
    acoustically coupling an ultrasound circuit to both a lens and a sample of the instrument, the ultrasound circuit comprising an ultrasound transmitter and an ultrasound receiver;
    configuring the ultrasound circuit to provide a first acoustic path, through a body of the instrument, when the lens and the sample are not both in direct contact with an immersion fluid of the instrument, and a second, shorter, acoustic path through the immersion fluid, when the lens and the sample are both in direct contact with the immersion fluid;
    transmitting an ultrasound pulse from the ultrasound transmitter to the ultrasound receiver;
    measuring a transit time of the ultrasound pulse;
    if the transit time is not less than a threshold time, determining that the ultrasound pulse was transmitted along the first acoustic path; and if the transit time is less than the threshold time, determining that the ultrasound pulse was transmitted along the second acoustic path.

2. The method of claim 1, further comprising providing an adjustment mechanism able to control a distance between the lens and the sample, and controlling the adjustment mechanism based on the measured transit time of the ultrasound pulse.

3. The method of claim 2, wherein said controlling the adjustment mechanism further comprises controlling the adjustment mechanism to automatically adjust the distance between the lens and the sample.

4. The method of claim 2, wherein said controlling the adjustment mechanism further comprises controlling the adjustment mechanism to automatically decrease the distance between the lens and the sample a preset distance after determining that the transit time is greater than the threshold time.

5. The method of claim 2, wherein said controlling the adjustment mechanism further comprises controlling the adjustment mechanism to automatically decrease the distance between the lens and the sample until the transit time is less than the threshold time.

6. The method of claim 1, further comprising providing, from a pulse discriminator, an output signal indicating that the transit time of the ultrasound pulse is less than the threshold time, wherein the output signal further indicates that the lens and the sample are both in direct contact with the immersion fluid.

7. The method of claim 6, further comprising providing a status confirmation in response to the output signal confirming that the lens and the sample are both in direct contact with the immersion fluid.

8. The method of claim 1, wherein the threshold time is between 15 µS and 25 µS.

9. A method for controlling lens immersion in an instrument, the method comprising:
acoustically coupling an ultrasound circuit to both a lens and a sample of the instrument, the ultrasound circuit comprising an ultrasound transmitter and an ultrasound receiver;
transmitting an ultrasound pulse from the ultrasound transmitter to the ultrasound receiver wherein the ultrasound pulse travels through an immersion fluid in contact with both the lens and the sample;
measuring an amplitude of the ultrasound pulse;
providing an adjustment mechanism able to control a distance between the lens and the sample; and
if the measured amplitude is greater than a threshold amplitude, controlling the adjustment mechanism to adjust the distance between the lens and the sample based on the measured amplitude of the ultrasound pulse.

10. The method of claim 9, further comprising controlling the adjustment mechanism to automatically adjust the distance between the lens and the sample based on the measured amplitude of the ultrasound pulse.

11. The method of claim 10, wherein said controlling the adjustment mechanism further comprises controlling the adjustment mechanism to automatically increase the distance between the lens and the sample a preset distance after determining that the measured amplitude is greater than the threshold amplitude.

12. The method of claim 10, wherein said controlling the adjustment mechanism further comprises controlling the adjustment mechanism to automatically increase the distance between the lens and the sample slide until the measured amplitude is less than the threshold amplitude.

13. The method of claim 9, further comprising providing an output signal to indicate that the amplitude for the ultrasound pulse is greater than the threshold amplitude.

14. A method for automatically focusing an instrument, the method comprising:
acoustically coupling an ultrasound circuit to both a lens and a sample of the instrument, the ultrasound circuit comprising an ultrasound transmitter and an ultrasound receiver,
transmitting an ultrasound pulse from the ultrasound transmitter to the ultrasound receiver, wherein the ultrasound pulse travels through an immersion fluid in contact with both the lens and the sample;
determining a distance between the lens and the sample based on the ultrasound pulse;
providing an adjustment mechanism able to control a distance between the lens and the sample; and
if the determined distance between the lens and the sample is different than a threshold distance, controlling the adjustment mechanism to automatically adjust the distance between the lens and the sample and enable automatic focusing of the lens with respect to the sample.

15. The method of claim 14, wherein the instrument is an optical microscope and the lens is an objective lens.

16. The method of claim 14, wherein the ultrasound pulse comprises a single frequency pulse or a spectral pulse comprising a spectrum of different frequencies.

17. The method of claim 16, wherein the ultrasound pulse comprises a single frequency pulse, and wherein determining the distance between the lens and the sample further comprises measuring a decay of the ultrasound pulse as the ultrasound pulse travels through the immersion fluid.

18. The method of claim 16, wherein the ultrasound pulse comprises a spectral pulse, and wherein determining the distance between the lens and the sample further comprises measuring an attenuation of frequencies in the spectral pulse as the spectral pulse travels through the immersion fluid.

19. An instrument comprising:
a lens;
a holder configured to receive a sample;
an immersion fluid deposited on at least one of the lens and the sample;
an ultrasound circuit acoustically coupled to the lens and the sample in the holder, the ultrasound circuit comprising an ultrasound transmitter and an ultrasound receiver, wherein the ultrasound circuit is configured to provide a first acoustic path when the lens and the sample are not both in direct contact with the immersion fluid, and a second, shorter, acoustic path through the immersion fluid, when the lens and the sample are in direct contact with the immersion fluid; and
an adjustment mechanism configured to control a distance between the lens and the sample.

20. The instrument of claim 19, further comprises a pulse discriminator electrically coupled to the ultrasound circuit, wherein the pulse discriminator is configured to determine that, if a measured transit time of the ultrasound pulse is greater than a threshold time, the ultrasound pulse was transmitted along the first acoustic path; and that if the measured transit time is less than the threshold time, the ultrasound pulse was transmitted along the second acoustic path.

21. The instrument of claim 19, wherein the adjustment mechanism is configured to automatically decrease the distance between the lens and the sample a preset distance until a measured transit time is less than the threshold time.

22. The instrument of claim 19, further comprises a pulse discriminator electrically coupled to the ultrasound circuit, wherein the pulse discriminator is configured to determine whether the ultrasound pulse has an amplitude greater than a threshold amplitude, and wherein the threshold amplitude indicates that the lens is in direct contact with the sample.

23. The instrument of claim 19, wherein the adjustment mechanism is configured to adjust the distance between the lens and the sample based on a measured amplitude of the ultrasound pulse.

24. The instrument of claim 19, wherein the adjustment mechanism is configured to automatically adjust the distance between the lens and the sample and enable automatic focusing of the lens with respect to the sample.

25. The instrument of claim 19, wherein the ultrasound transmitter is directly coupled to the lens.

26. The instrument of claim 19, wherein the ultrasound receiver is directly coupled to the lens.

* * * * *